US008740793B2

(12) United States Patent
Cuddihy et al.

(10) Patent No.: US 8,740,793 B2
(45) Date of Patent: Jun. 3, 2014

(54) RADAR BASED SYSTEMS AND METHODS FOR MONITORING A SUBJECT

(75) Inventors: Paul Edward Cuddihy, Ballston Lake, NY (US); Daniel Joseph Cleary, Schenectady, NY (US); Jeffrey Michael Ashe, Gloversville, NY (US); Tarik Yardibi, Schenectady, NY (US)

(73) Assignee: General Electric Company, Niskayuna, NY (US)

( * ) Notice: Subject to any disclaimer, the term of this patent is extended or adjusted under 35 U.S.C. 154(b) by 264 days.

(21) Appl. No.: 13/219,779

(22) Filed: Aug. 29, 2011

(65) Prior Publication Data

US 2013/0053653 A1 Feb. 28, 2013

(51) Int. Cl.
*A61B 5/00* (2006.01)
*G06F 19/00* (2011.01)

(52) U.S. Cl.
CPC ............................. *G06F 19/3418* (2013.01)
USPC ........................................................ 600/301

(58) Field of Classification Search
USPC ................................................ 600/300–301
See application file for complete search history.

(56) References Cited

U.S. PATENT DOCUMENTS

| | | | |
|---|---|---|---|
| 6,569,092 B1* | 5/2003 | Guichon et al. .............. 600/300 |
| 7,567,200 B1 | 7/2009 | Osterweil | |
| 7,671,784 B2* | 3/2010 | Steinway et al. ............... 342/22 |
| 8,052,600 B2* | 11/2011 | Beck et al. .................... 600/301 |
| 8,410,926 B1* | 4/2013 | Gary et al. ............... 340/539.12 |
| 8,562,526 B2* | 10/2013 | Heneghan et al. ............ 600/301 |
| 2002/0010390 A1* | 1/2002 | Guice et al. ................... 600/300 |
| 2005/0073424 A1* | 4/2005 | Ruoss et al. ................ 340/686.6 |
| 2008/0269589 A1 | 10/2008 | Thij's et al. | |
| 2008/0275337 A1 | 11/2008 | Fossan et al. | |
| 2009/0203972 A1* | 8/2009 | Heneghan et al. ............. 600/301 |
| 2010/0041966 A1* | 2/2010 | Kang et al. .................... 600/301 |
| 2010/0204550 A1* | 8/2010 | Heneghan et al. ............. 600/301 |
| 2011/0144455 A1* | 6/2011 | Young et al. ................... 600/301 |

(Continued)

FOREIGN PATENT DOCUMENTS

| | | |
|---|---|---|
| WO | 2008121448 A2 | 10/2008 |
| WO | 2009136341 A1 | 9/2009 |
| WO | 2009136337 A1 | 11/2009 |
| WO | 2010132850 A1 | 11/2010 |

OTHER PUBLICATIONS

Sanghyun Chang, Naoki Mitsumoto and Joel W. Burdick; "An algorithm for UWB radar-based human detection"; 978-1-4244-2871-7/09/$25.00 © 2009 IEEE; vol. 33 issue 1, pp. 1-6.

(Continued)

*Primary Examiner* — Gary Jackson
*Assistant Examiner* — Bobby Soriano
(74) *Attorney, Agent, or Firm* — Scott J. Asmus

(57) ABSTRACT

Methods and systems for monitoring a subject in a resting state using one or more range-controlled radars are presented. The radars non-invasively detect one or more motion and/or physiological parameters corresponding to the subject. The motion parameters comprise one or more activity levels and the physiological parameters comprise one or more of heartbeat and respiration. Further, one or more patterns in the motion parameters detected over a designated motion period of time are determined. Additionally, one or more patterns in the physiological parameters detected over the designated physiological period of time are also determined. The systems then assess a health condition of the subject based on the determined patterns of the motion parameters and/or the determined patterns of the physiological parameters.

20 Claims, 3 Drawing Sheets

(56) References Cited

U.S. PATENT DOCUMENTS

2011/0263950 A1* 10/2011 Larson et al. ............... 600/301
2012/0245439 A1*  9/2012 Andre et al. ............... 600/310
2012/0271372 A1* 10/2012 Osorio ........................ 607/17

OTHER PUBLICATIONS

Po Li and De-Chun Wang; "A Quadrature Doppler Radar System for Sensing Human Respiration and Heart Rates"; Signal Processing (ICSP), 2010 IEEE 10th International Conference; pp. 2235-2238.
Paul Edward Cuddihy; "Method and System for Fall Detection"; filed Jun. 21, 2010; U.S. Appl. No. 12/819,260; 28Pages.
Paul Edward Cuddihy et al.; "Method and System for Detecting a Fallen Person Using a Range Imaging Device"; filed Jul. 30, 2010; U.S. Appl. No. 12/847,321; 30Pages.
Meena Ganesh et al; "Physiology Monitoring and Alerting System and Process"; filed Mar. 23, 2011; U.S. Appl. No. 13/069,483.
Paul Edward Cuddihy et al; "Radar Based Systems and Methods for Detecting a Fallen Person"; U.S. Appl. No. 13/173,489, filed Jun. 30, 2011.

* cited by examiner

RADAR BASED SYSTEMS AND METHODS FOR MONITORING A SUBJECT

BACKGROUND

Embodiments of the present technique relate generally to health monitoring, and more particularly to radar based methods and systems for monitoring a person in a resting state.

Sound sleep is generally beneficial and restorative for a person's health and exerts a great influence on the quality of life of the person. The human sleep/wake cycle typically conforms to a circadian rhythm regulated by a biological clock. The sleep cycle of a healthy person, for example, is characterized by a general decrease in metabolic rate, body temperature, blood pressure, breathing rate, heart rate, cardiac output, sympathetic nervous activity and other physiological functions. Accordingly, changes in such physiological parameters owing to disturbed or poor sleep quality are often indicative of deteriorating health of the person.

Monitoring sleep and wake patterns and various physiological parameters such as heart rate and respiration during sleep, thus, provides clinical markers for identifying and treating various health conditions afflicting a subject. These health conditions, for example, include insomnia, obstructive sleep apnea and central sleep apnea. Obstructive sleep apnea collapses the upper airway, thus restricting the flow of air to the lungs even in the presence of an ongoing respiratory effort, while also causing detrimental changes in the subject's heart rate. Central sleep apnea, however, results in a complete loss of respiratory effort leading to a loss of air to the lungs and eventually lowering the oxygen in the blood.

Other common sleep disorders in adults include conditions such as Periodic Limb Movements Disorder (PLMD) and Restless Legs Syndrome (RLS). In PLMD, the subject makes characteristic repetitive movements every 30-40 seconds leading to sleep disruption. In RLS, the subject has an overwhelming desire to move or flex their legs as they fall asleep, again leading to disrupted sleep patterns. Accordingly, monitoring such anomalous body movements during the resting state is useful in identifying and treating various heath conditions of the subject.

To that end, a clinically accepted sleep diagnostic technique employs a sleep laboratory, where the subject is connected to a polysomnography (PSG) machine that records multiple physiological parameters. A sleep laboratory evaluation, however, requires the subject to be tethered to multiple cables with electrodes attached to their torso and head, often resulting in disruptive sleep patterns due to anxiety and/or physical discomfort. Particularly in the case of children (pediatrics), it is exceedingly difficult to assure connections well enough to assess sleep health. Additionally, the use of such complex and intrusive equipment necessitates monitoring the subject at a dedicated testing facility with trained technicians, often costing over a thousand dollars per night.

Certain other sleep monitoring systems employ air bladders, vibration and other electronic and motion sensors disposed in a mattress or bed of the subject to monitor the subject's movements and sleep patterns. These systems, however, require use of customized beds and mattresses that may not suit the subject's comfort or liking. Furthermore, these systems are often unable to prevent gross motion of the subject from affecting the heartbeat and respiration readings leading to inaccurate measurements. Accordingly, certain companies have employed rather complex radar systems for non-contact pulse and respiration measurements for short term monitoring. Many of these sensors and systems, however, incur inhibitive cost and complexity for monitoring the subject continuously.

It is desirable to develop unobtrusive and cost-effective methods and systems for monitoring a person in a resting state. Specifically, there is a need for efficient sleep monitoring systems and methods that non-intrusively yet reliably measure various motion and physiological parameters to determine sleep metrics corresponding to the subject. Furthermore, it is desirable to develop systems that do not require contact or line-of-sight to the subject's body and are capable of accurately assessing the health of the subject.

BRIEF DESCRIPTION

Certain aspects of the present technique are drawn to methods for monitoring a subject in a resting state using one or more range-controlled radars are presented. The radars non-invasively detect one or more motion and/or physiological parameters corresponding to the subject. The motion parameters comprise one or more activity levels and the physiological parameters comprise one or more of heartbeat and respiration. Further, one or more patterns in the motion parameters detected over a designated motion period of time are determined. Additionally, one or more patterns in the physiological parameters detected over the designated physiological period of time are also determined. The systems then assess a health condition of the subject based on the determined patterns of the motion parameters and/or the determined patterns of the physiological parameters.

Another aspect of the present technique includes a system for non-contact monitoring of a subject. The system includes one or more range-controlled radars configured to transmit a radar signal and receive a reflected radar signal from the subject in a resting state. Further, the system also includes at least one processing unit communicatively coupled to the one or more range-controlled radars. The processing unit is configured to non-invasively detect one or more motion and/or physiological parameters corresponding to the subject using the one or more range-controlled radars. The motion parameters comprise one or more activity levels and the physiological parameters comprise one or more of heartbeat and respiration. The processing unit determines one or more patterns in the motion parameters detected over a designated motion period of time. Additionally, the processing unit determines one or more patterns in the physiological parameters detected over the designated physiological period of time. The processing unit then assesses a health condition of the subject based on the determined patterns of the motion parameters and/or the determined patterns of the physiological parameters. The system further includes a data repository coupled to the processing unit to store one or more of the reflected radar signal data, the motion parameters, the physiological parameters and/or the determined patterns.

A further aspect of the present technique corresponds to non-transitory computer readable media that store instructions executable by one or more processors to perform a method for monitoring a subject in a resting state using one or more range-controlled radars are presented. The processors execute instructions for non-invasively detecting one or more motion and/or physiological parameters corresponding to the subject. The motion parameters comprise one or more activity levels and the physiological parameters comprise one or more of heartbeat and respiration. Further, the processors detect one or more patterns in the motion parameters over a designated motion period of time are determined. Additionally, one or more patterns in the physiological parameters detected over the designated physiological period of time are also determined. The processors then execute instructions that allow assessment of a health condition of the subject based on the determined patterns of the motion parameters and/or the determined patterns of the physiological parameters One technical effect of the methods and systems of the present disclosure is for non-contact monitoring of a subject in a resting state using one or more range-controlled radars. In particular, a technical effect allows a monitoring system to non-invasively detect one or more motion and/or physiological parameters and assess a health condition of the subject based on determined patterns of the detected motion parameters and/or the physiological parameters.

DRAWINGS

These and other features, aspects, and advantages of the present technique will become better understood when the following detailed description is read with reference to the accompanying drawings in which like characters represent like parts throughout the drawings, wherein.

DETAILED DESCRIPTION

The following description presents systems and methods for assessing a health condition of a subject, for example a person, by non-intrusively monitoring the subject in a resting state. Particularly, certain embodiments illustrated herein describe inexpensive yet efficient methods and systems that monitor the subject in the resting state using one or more range-controlled RADAR (Radio Detection and Ranging) systems. As used herein, the term "resting state" corresponds to a state of the subject, in which the subject typically exhibits negligible or insignificant motion, such as when the subject is sleeping, resting, relaxing, or meditating. Although there may be some movement that may occur during such resting state in a healthy subject, such movement is generally considered insignificant. In certain embodiments, the subject monitored by the range-controlled radar is supine and oriented on a surface such as, for example, a bed, floor, couch, or chair during the resting state. Furthermore, the term "range-controlled" RADAR refers to a radar that limits an associated transmit interval and/or a receive interval in order to process only those signals that are received by a corresponding antenna from a designated radial range.

Although the present systems describe use of range-controlled RADAR circuitry, the systems may include any other suitable type of motion sensing devices, such as electromagnetic, acoustic or optical measurement devices for monitoring the subject in different operating environments. An exemplary environment that is suitable for practicing various implementations of the present systems and methods is described in the following sections with reference to FIG. 1.

Figure 1:
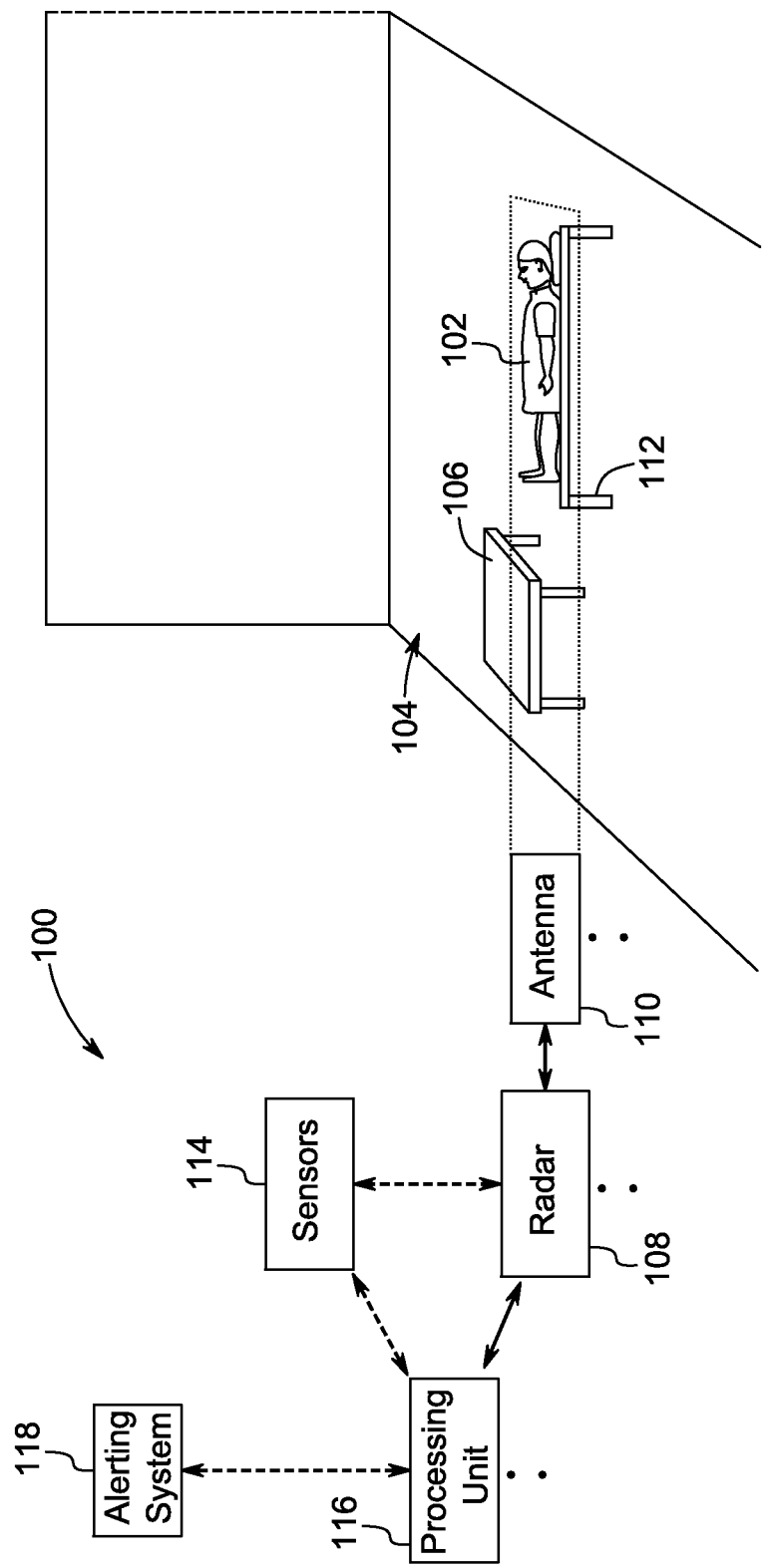
FIG. 1 is a block diagram of an exemplary system for monitoring a subject in a resting state, in accordance with aspects of the present system.

FIG. 1 illustrates an exemplary health monitoring system 100 for contact-less monitoring of a subject 102 such as a person or an animal in a resting state. In the present description, variations of the terms "non-intrusive," "non-invasive" and "contact-less" monitoring are used interchangeably to refer to observing and/or measuring one or more parameters associated with the subject 102 with no or negligible direct physical contact with the subject 102. Particularly, the system 100 monitors the subject 102 resting in a designated space 104, such as a room in an assisted living facility or a hospital bed, for assessing a health condition of the subject 102. The designated space 104, for example, may further include one or more objects 106, such as chairs, beds, tables, columns and cupboards. In certain scenarios, these objects 106 obstruct the direct line-of-sight between the system 100 and one or more portions of the designated space 104 where the subject 102 may be resting.

Accordingly, the system 100 includes a radar system 108 coupled to an antenna 110 for non-intrusively monitoring the subject 102, for example, resting on a bed 112 in the designated space 104. An advantage of using the radar system 108 for monitoring the subject 102 as opposed to using video-based monitoring systems includes the ability to provide operational capability even in the presence of certain obstructions in the designated space 104. To that end, the radar system 108 includes suitable devices such as microwave impulse radar ("MIR"), range-controlled radar ("RCR"), impulse radio and microwave Doppler devices, which, in one embodiment, are appropriately range-gated to detect motion of the subject 102 within the designated space 104.

In certain embodiments, the radar system 106 is calibrated for optimal monitoring performance by establishing range settings according to the shape and size of a surface, such as the bed 112 or a chair (not shown) on which the subject 102 is resting. In one implementation, for example, the radar system 108 allows selection from a plurality of range settings, such as about 5 feet, 10 feet and 15 feet to focus on a desired potion of the designated space 104. Further, unlike conventional microwave sensors that may erroneously detect other subjects in adjoining areas, selection of a desired range setting allows the radar system 108 to detect the subject 102 disposed in the desired portion.

In one embodiment, for example, the range-gated radar system 108 monitors the subject 102 relaxing or sleeping on the bed 112 disposed in the designated space 102, while ignoring subjects, for example, in other portions of the room or outside. To that end, the radar system 108 is appropriately positioned in the designated space 104 to effectively monitor the subject 102 disposed in the designated space 102. In one embodiment, the radar system 108 is positioned at the head/foot of the bed 112 or proximate the chair (not shown) on which the subject 102 is resting. In certain embodiments, the radar system 108 may be positioned on a table or wall adjacent or opposite the bed 112, or on the ceiling of the room to monitor the subject 102. Additionally, in certain embodiments, the system 100 includes a passive infrared (PIR) motion sensor (not shown) coupled to the radar 108. The PIR motion sensor activates and/or deactivates the radar 108 based on a presence or an absence of motion in the designated space 104, thus saving power and reducing the radio frequency (RF) signal transmission.

While monitoring the subject 102, the radar system 108 transmits electromagnetic signals towards the desired portions of the designated space 104 such as the bed 112 and senses corresponding echo signals reflected from the subject 102 disposed on the bed 112. To that end, in certain embodiments, the system 100 employs the directional antenna 110 coupled to the radar system 108 to constrain the radar signal over the desired portions of the designated space 104 where the subject 102 is resting. More particularly, the radar system 108 employs the antenna 110 to transmit and receive one or more pulse sequences that are sensitive to not only gross body motion but also physiological motion such as heartbeat and respiration of the subject 102.

In one embodiment, for example, the radar system 108 transmits two pulses at a high repetition rate (on the order of 5 MHz) for a carrier in the 5.8 GHz ISM band for monitoring movements of the subject 102. The radar system 108 then receives signals reflected from subject 102 and determines one or more motion and physiological parameters of the subject 102 using the received signals. If the system 100 fails to detect one or more of motion and/or physiological parameters, in one implementation, the subject 102 is assumed to be out of range. If the subject 102 is within range, the system 100 extracts data corresponding to the subject's gross motion, respiration and/or heartbeat to determine the subject's health condition.

In certain scenarios, certain additional parameters such as ambient temperature, humidity, light and sound levels may affect the motion and physiological parameters of the subject 102. Accordingly, in one embodiment, the system 100 further includes one or more sensors 114 for measuring additional parameters that may affect the state of the subject 102. To that end, the sensors 114, for example, include an acoustic sensor, an infrared body temperature sensor, and other sensors that measure parameters such as ambient humidity, temperature and light level. The system 100 uses these additional parameters along with the determined motion and physiological parameters to assess a health condition of the subject 102.

To that end, in one embodiment, the system 100 includes one or more processing units 116 coupled to the radar system 108 to ascertain the health of the subject 102 based on the reflected radar signals and/or the sensor measurements. In one embodiment, for example, the processing unit 116 filters the reflected radar signals to extract motion, heartbeat and respiration data into signal frames based on their corresponding frequency band characteristics. The processing unit 116 then uses the extracted values to determine a health condition of the subject 102.

By way of example, the processing unit 116 uses the duration and frequency of detected motion events to determine the level of restlessness or disturbance experienced by the subject 102 in the resting state. Further, the processing unit 116 performs spectral evaluation of the extracted heartbeat and respiration frames to determine if the subject 102 is suffering from conditions such as arrhythmia, bradycardia, tachycardia, bradypnea, tachypnea and/or apnea. In certain embodiments, the processing unit 116 evaluates the determined motion, heartbeat and respiration data in light of the information measured by sensors 114 such as ambient light, sound, temperature and humidity levels to make a more accurate assessment of the subject's health.

Further, in one embodiment, the processing unit 116 monitors the subject 102 over a designated period of time and stores the corresponding motion, heartbeat and respiration data for further evaluation. In certain embodiments, the motion, respiration and heartbeat data captured and stored when the subject 102 is healthy is used as a baseline for evaluation. In another embodiment, the processing unit 116 uses the motion, respiration and heartbeat data captured and stored when the subject 102 is unhealthy as a baseline for evaluating improvement and/or degradation of the subject's health. The processing unit 116 uses the baseline data, for example, to ascertain how a drug, treatment, physical activity or any other stimulus provided to the subject 102 affects the health condition of the subject 102 over the designated period of time.

Typically, conditions such as apnea, bradycardia and tachycardia exist along with impaired heart function. Accordingly, in one implementation, the processing unit 116 compares the measured heartbeat and respiration data with corresponding baseline values for early detection of changes in cardiac function that indicate an increased risk of heart disease. In another implementation, the processing unit 116 compares the measured motion, heartbeat and respiration values with corresponding baseline information to detect if the subject's resting state includes active stages including rapid eye movement (REM) sleep and passive 1, 2, 3, 4 and 5 sleep stages. Particularly, unobtrusive monitoring using the system 100 allows the processing unit 116 to quantify how much and how often, the motion, respiration and heartbeat patterns change over the designated period of time. The changes in these patterns, in turn, can be used to identify and monitor conditions such as dementia, which are known to disrupt circadian rhythms.

Additionally, in certain embodiments, the processing unit 116 evaluates the changes for tracking recovery, medication effects, or predicting increased risk of impending health impairment. By way of example, the processing unit 116 evaluates the changes and aids a medical practitioner in recommending specific sleep hygiene for monitoring subjects suffering from traumatic brain injury (TBI) or post-traumatic stress disorder (PTSD), who rarely experience "regular" periods of sleep. The specified sleep hygiene aims to mitigate certain behavioral and environmental factors that precede sleep and may interfere with the subject's sleep. The processing unit 116, thus, provides information to aid in adapting the treatment and suggesting behavior that benefits the health of the subject 102.

However, if the processing unit 116 determines that the health of the subject 102 is deteriorating, in certain embodiments, the processing unit 116 triggers an alert through an alerting system 118 coupled to the radar system 108 and/or the processing subsystem 116. The processing unit 116, for example, may generate and alert if the detected heartbeat and/or respiration values of an infant remain outside corresponding threshold values for more than a determined period of time. The alerting system 118, for example, generates an audio output and/or a visual output such as flashing lights, display messages and/or an alarm. Additionally, the alerting system 118 can also sound an alarm, send a voicemail, text message and/or email to a mobile device of appropriate personnel and/or to another monitoring system through a wired and/or wireless link.

Although the system provides for non-invasive monitoring as detailed herein, in certain embodiments, the system can be present with other devices and systems that can be non-invasive and/or invasive and provide additional data that can be processed by the processing units or by some central processing section to enable more comprehensive monitoring, assessment, diagnosis, and/or preventative care. The structure and functioning of an exemplary system for monitoring a designated space and assessing a health condition of the subject 102, in accordance with aspects of the present technique, is described in greater detail with reference to FIGS. 2-3.

Figure 2:
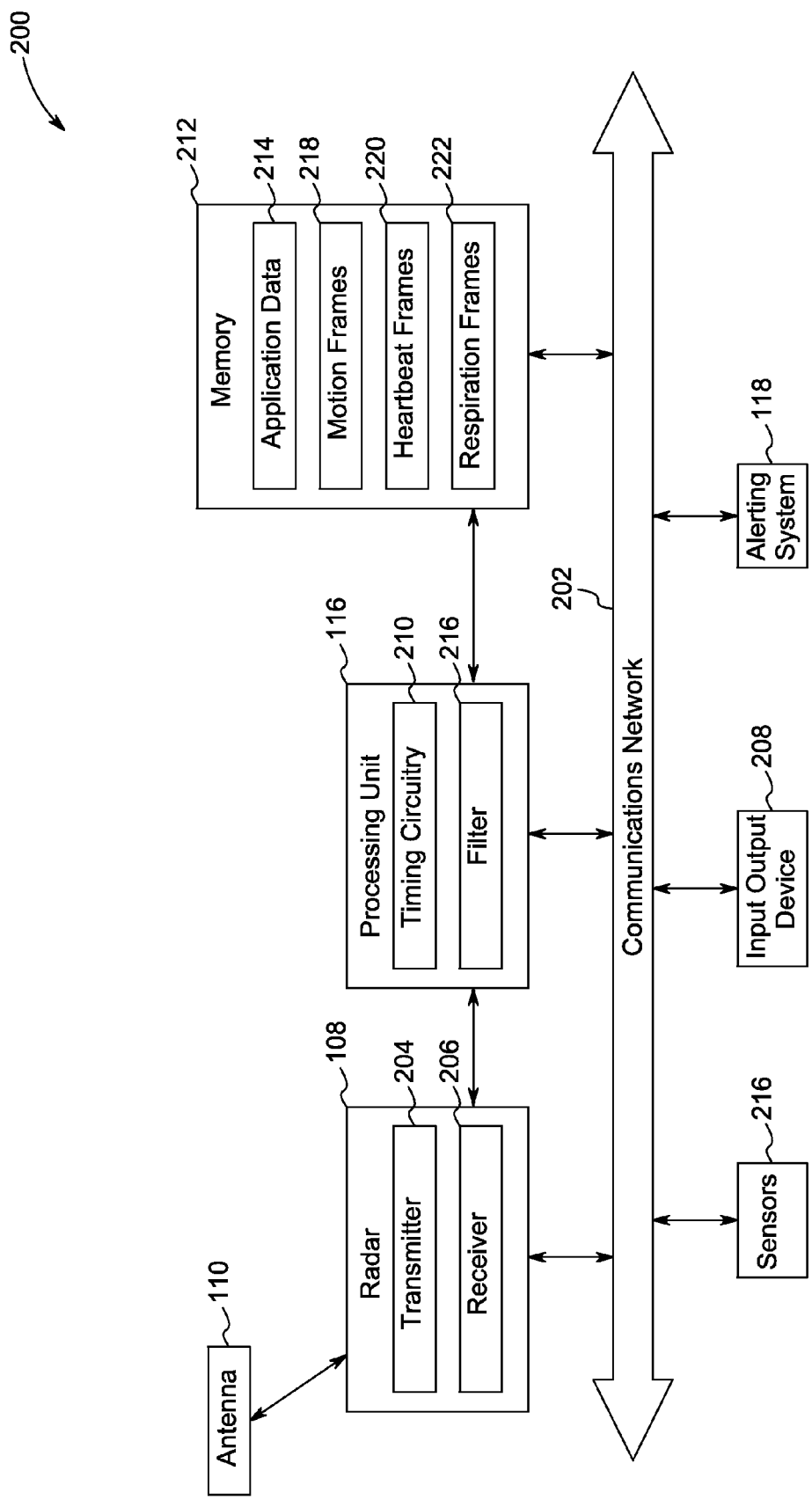
FIG. 2 is a block diagram of another exemplary system for monitoring the subject in the resting state, in accordance with aspects of the present system.

FIG. 2 illustrates another embodiment of the health monitoring system 100 of FIG. 1 for monitoring the subject 102 in a resting state. In one embodiment, the system 100 includes the range-gated radar 108 coupled to the planar antenna 110 and the one or more processing units 116 over a communications network 202. To that end, the communication network 202 includes, for example, wired networks such as LAN and cable, and/or wireless networks such as WLAN, cellular networks, satellite networks, and short-range networks such as ZigBee wireless sensor networks. In particular, the communication network 202 allows transmission of signal data received by the radar 108 to the processing unit 116 for further processing and evaluation.

As previously noted, the radar system 108 transmits electromagnetic signals and senses the echo from objects in the designated space 104, thus gaining information about the motion of the objects. To that end, in one embodiment, the radar 108 includes a transmitter 204 and a receiver 206. The transmitter 204 generates and amplifies a signal waveform to a required transmission power. Optionally, the transmitter 204 filters the signal before transmission to prevent inclusion of any extraneous signals.

Additionally, the antenna 110 focuses the radar signal transmitted by the transmitter 204 over a desired portion of the designated space 104. To that end, the antenna 110, for example, includes a dipole antenna, a patch antenna, a parabolic antenna or any antenna that provides directivity. Specifically, in one embodiment, the antenna 110 is a directional antenna that focuses the radar signal over the desired portion, for example, a floor or the bed 112 disposed in the designated space 104 where the subject 102 is resting.

Further, the receiver 206 receives and processes the radar signals reflected from the objects 106 in the designated space 104 for further use. The receiver 206, for example, converts the signal from the transmission frequency to an intermediate or baseband frequency, segregates the signal information from noise and interference, and/or appropriately amplifies the signal for digitization and/or display. In certain embodiments, the processing unit 116 evaluates the movements of the subject 102 in the designated space 102 using the signals received and/or processed by the receiver 206. In particular, the processing unit 116 evaluates the signals reflected from surfaces, for example, a chest wall of the subject 102 in the resting state to identify movements associated with the subject 102.

To that end, the system 100 employs the planar antenna 110 focused over the desired portion of the designated space 104 to capture motion and other physiological parameters corresponding to the subject 102. In certain embodiments, the system 100 includes an input-output device 208, such as a graphical user interface (GUI), to allow a user to configure the radar 108 and antenna 110 settings to focus over different portions of the designated space 104. The input-output device 208 allows the user to configure the system 100 to change focus to an appropriate portion of the designated space 104 in case the subject 102 changes his or her resting potion, for example, from the bed 112 to the floor.

Further, the processing unit 116, coupled to the radar 108, evaluates the signals received from the radar 108 to determine the subject's movements. In one embodiment, the subject 102 is assumed to be out of range if the radar system 108 focused over a desired portion fails to detect one or more of motion and/or physiological parameters. If the subject 102 is within range, the processing unit 116 extracts data corresponding to the subject's gross motion, respiration and heartbeat from the reflected signal data to determine the subject's health condition. To that end, the processing unit 116 includes, for example, one or more microprocessors, microcomputers, microcontrollers, and so forth, for evaluating the reflected signal data. In one embodiment, the processing unit 116 identifies and extracts gross motion data from the received signals. If gross motion is not detected, the processing unit 116 identifies and extracts data corresponding to physiological parameters such as heartbeat and respiration from the received signals. In an alternative embodiment, however, the processing unit 116 extracts the gross motion, heartbeat and respiration data from the received signals.

The processing unit 116, in certain embodiments, stores the extracted gross motion, heartbeat and respiration data along with the received radar signals in a data repository or memory 212, such as RAM, ROM, disc drive or flash memory as application data 214. The processing unit 116 may also store antenna and radar settings, heartbeat, respiration and gross motion thresholds and corresponding characteristics and patterns indicative of known ailments as application data 214. In certain embodiments, the processing unit 116 extracts characteristics and patterns from the gross motion, heartbeat and respiration data captured by monitoring the subject 102 over a period of time.

To that end, in one embodiment, the processing unit 208 includes timing circuitry 210 to determine a time, duration and/or frequency of movements associated with the subject 102 during a designated period of time. In certain embodiments, the processing unit 116 stores the timing and frequency information in the memory 212 for later evaluation. In one exemplary evaluation, the processing unit 116 identifies the presence of gross motion outside certain designated limits as sleep disturbance. To that end, the designated limits can be pre-programmed into the system 100, input by a user or learned by the system 100 over a period of time.

Further, the time, the duration and the frequency of disturbance while sleeping or in the resting state provides an indication of the nature and/or the extent of the anomalous behavior exhibited by the subject 102. The nature and extent of the anomalous behavior, in turn, allows the processing unit 116 to determine if the person is suffering from a specific health condition, such as RLS or PLMD. In one embodiment, for example, the processing unit 116 compares the detected time and frequency of sleep disturbance, heartbeat and respiration data with the stored motion, heartbeat and respiration characteristics and patterns indicative of known ailments. Alternatively, the processing unit 116 uses the subject's average heartbeat, respiration and motion characteristics evaluated over the designated period of time to identify if the subject is suffering from a known ailment.

To that end, the processing unit 116, for example, employs a filter element 216 that generates a signal frame of a particular time duration from the reflected radar signals. Particularly, in one embodiment, the filter element 216 generates motion frames 218, heartbeat frames 220 and respiration frames 222 from the received radar signals based on corresponding frequency band characteristics. By way of example, the filter element 216 generates the motion or high band frame corresponding to a signal of about 4 Hz to about 10 Hz, the heartbeat or mid band frame corresponding to a signal of about 1 Hz to about 2 Hz, and the respiration or low band frame corresponding to a signal just above 0.1 Hz to about 0.5 Hz. Accordingly, in certain embodiments, the filter element 216 includes low pass and/or band pass filters that extract the motion frames 218, the heartbeat frames 220 and the respiration frames 222 from each signal frame.

The processing unit 116, in certain embodiments, extracts statistical, spectral and/or temporal features from the extracted frames. These features include, for example, a minimum, maximum, average and root mean square (RMS) values of amplitude and/or frequency associated with the motion frames 218, the heartbeat frames 220 and the respiration frames 222. In one embodiment, the average frequency features are used to provide estimates of the rates associated with the detected physiological parameter such as the rate of respiration and heartbeat rate. Further, the RMS amplitude features may be used to provide estimates of the strengths associated with the detected physiological parameter such as the depth of respiration or the degree of the subject's motion.

The processing unit 116 uses the extracted features and estimated rates and values for identifying a health condition of the subject 102. The processing unit 116, for example, uses the extracted breathing rate or pattern to determine if the subject 102 is suffering from bradypnea (slow breathing), tachypnea (fast breathing), apnea (interrupted breathing) or cardiac pulmonary respiratory disease that require increased respiratory effort. Similarly, the processing unit 116 uses the determined heart rate and motion to identify underlying health conditions such as bradycardia (slow heartbeat), tachycardia (fast heartbeat), arrhythmia (irregular heartbeat) and/or sleep fragmentation.

The accurate assessment of the health condition of the subject 102, however, depends upon the accurate heartbeat and respiration readings. In conventional radar systems, presence of gross body motion during monitoring may corrupt the heartbeat and respiration estimates. Particularly, the conventional radar systems lacking sophisticated circuitry often include no reliable mechanism to distinguish between movement caused by gross motion and the movement caused by the physiological parameters, thus affecting the corresponding estimates. The present system 100, however, employs state estimation techniques that evaluate the heartbeat and respiration data in view of the presence or absence of gross motion.

In one embodiment, for example, the state estimation techniques employed by the processing unit 116 identify time periods including gross motion as sleep restlessness. The processing unit 116 further disregards any heartbeat and respiration data acquired during such periods of sleep restlessness during health assessment. In an alternative embodiment, however, the processing unit 116 assigns a weighted value to the heartbeat and respiration data acquired in presence of gross motion. The assigned weighted value is different from a value associated with the heartbeat and respiration data acquired in absence of gross motion to account at least in part for any variations in the detected values owing to the presence of gross motion.

Additionally, in certain embodiments, the processing unit 116 evaluates the captured gross motion, heartbeat and respiration data in light of additional parameters such as ambient environmental conditions and variations in the subject's activity levels. To that end, the system 100 includes the one or more sensors 114 for measuring the additional parameters that affect the subject's health. The sensors 114, for example, include an acoustic sensor, an infrared body temperature sensor, and other sensors that measure ambient humidity, temperature and light level.

By way of example, the ambient sound and temperature in the designated space 104 may affect the subject's respiration and sleep duration. Similarly, the subject's physiological parameters may be affected if the subject 102 begins a new fitness regime or starts use of a new medicine in between the period of monitoring. As these effects are independent of the health condition of the subject 102, in certain embodiments, the processing unit 116 accounts for the variations in the gross motion, heartbeat and respiration owing to these additional parameters. In one embodiment, for example, the processing unit 116 assigns weighted values to the gross motion, heartbeat and respiration data in view of the values of the additional parameter values. The specific weights assigned may be input by a user during use, preprogrammed into the system 100 or learned over a period of time. The processing unit 116 may also adjust the subject's physiological parameters in light of a known health condition or mental state of the subject 102.

The system 100 then uses these additional parameters and/or adjusted values of the determined motion and physiological parameters to assess the health condition of the subject 102. In certain embodiments, the processing unit 116 determines specific characteristics or patterns in these weighted, adjusted and/or actual values determined over a designated period of time. The processing unit 116 then compares the determined characteristics and patterns with stored motion, heartbeat and/or respiration patterns indicative of potential health conditions to identify if the subject 102 is suffering from a specific ailment such as apnea, arrhythmia or sleep disturbance.

Additionally, in certain embodiments, the processing unit 116 triggers an alert through the alerting system 118 coupled to the radar system 108 and/or the processing subsystem 116 on determining deterioration of the subject's health. By way of example, the processing unit 116 generates and/or communicates an audio and/or visual alert such as flashing lights, sounding an alarm and/or sending a text message through the alerting system 118 upon determining a progressive reduction in the heartbeat and/or respiration rates of the subject 102. The alerting system 118 communicates the alert through a wired and/or wireless link to appropriate personnel or a healthcare monitoring system for immediate assistance. Accordingly, in certain embodiments, the system 100 is implemented as a standalone system, for example in a mobile device, for monitoring the subject 102. Alternatively, the system 100 may be implemented as part of a larger healthcare system for monitoring the subject 102 and assessing the subject's health condition.

Use of the range-controlled radar based system 100, thus, allows for simple and uncomplicated processing for identifying a specific health condition of the subject based on presence or absence of gross motion, heartbeat and respiration and corresponding values. Particularly, the system 100 allows for more accurate assessment of the health condition of the subject based on whether the heartbeat and respiration readings of the subject are acquired in presence or absence of gross motion. An exemplary method for monitoring a subject in a designated space using range-controlled radar and for evaluating a health condition of the subject is described in greater detail with reference to FIG. 3.

Figure 3:
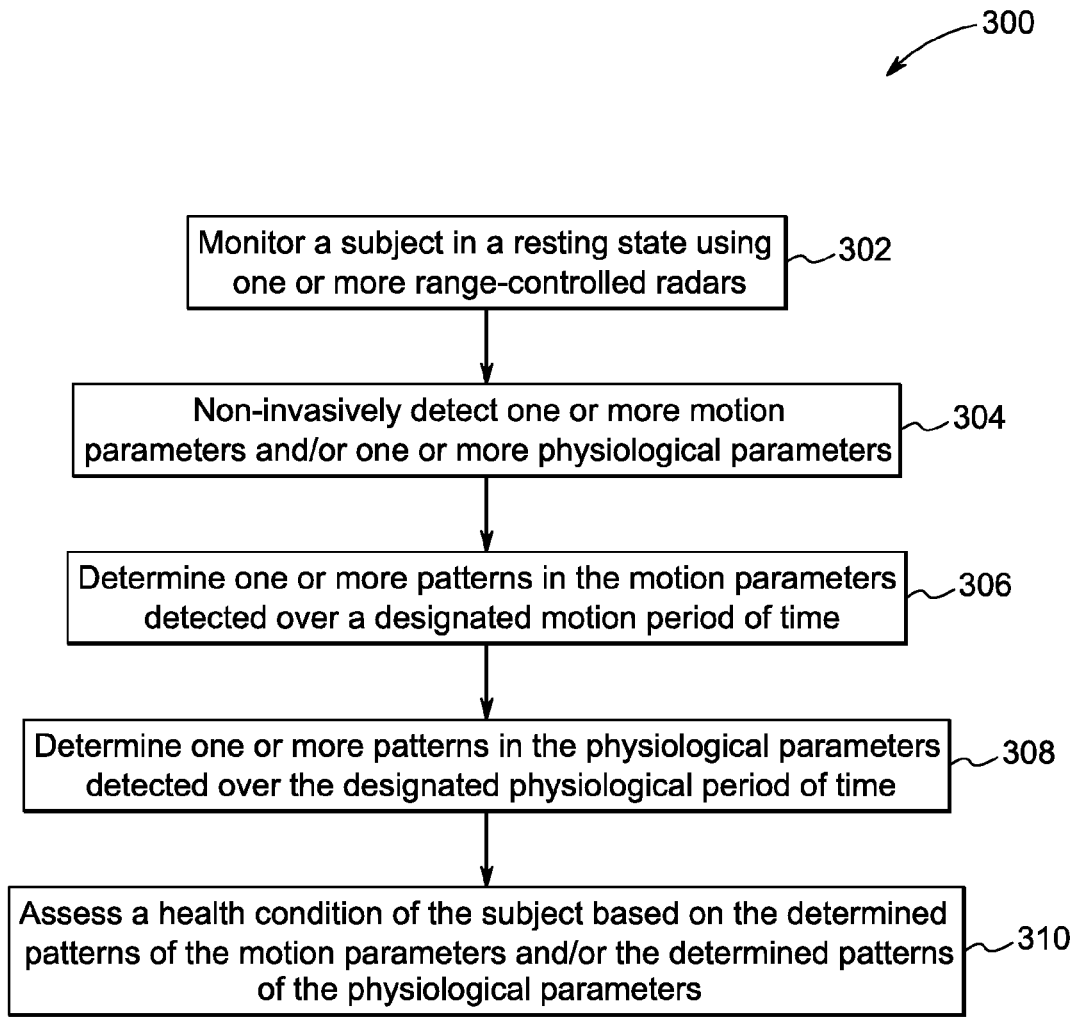
FIG. 3 is a flow chart illustrating an exemplary method for monitoring the subject in a resting state, in accordance with aspects of the present technique.

FIG. 3 illustrates a flow chart 300 depicting an exemplary method for monitoring a subject using a range-controlled radar system. The exemplary method may be described in a general context of computer executable instructions on a computing system or a processor. Generally, computer executable instructions may include routines, programs, objects, components, data structures, procedures, modules, functions, and the like that perform particular functions or implement particular abstract data types. The exemplary method may also be practiced in a distributed computing environment where optimization functions are performed by remote processing devices that are linked through a communications network. In the distributed computing environment, the computer executable instructions may be located in both local and remote computer storage media, including memory storage devices.

Further, in FIG. 3, the exemplary method is illustrated as a collection of items in a logical flow chart, which represents operations that may be implemented in hardware, software, or combinations thereof. In the context of software, the blocks represent computer instructions that, when executed by one or more processing subsystems, perform the recited operations. The order in which the exemplary method is described is not intended to be construed as a limitation, and any number of the described blocks may be combined in any order to implement the exemplary method disclosed herein, or an equivalent alternative method. Additionally, certain blocks may be deleted from the exemplary method without departing from the spirit and scope of the subject matter described herein. For discussion purposes, the exemplary method is described with reference to the implementations of FIGS. 1-2.

In one embodiment, a healthcare monitoring system, such as the system 100 of FIG. 2, continually monitors a subject resting in a designated space, such as a single hospital bed, a room, a chair or any other suitable space. As previously noted, the designated space, for example, includes one or more objects such as chairs, beds, tables, columns and cupboards that obstruct the direct line-of-sight between the system and one or more portions of the designated space. Accordingly, the system includes one or more range-controlled Doppler radars that can non-intrusively monitor a person in a sleeping or resting state in the designated space even in the presence of obstructions.

As previously noted, the term "resting state" corresponds to a state of the subject, in which the subject typically exhibits negligible motion, such as when the subject is asleep, meditating, or supine and relaxing on a surface such as a bed, floor or a chair. For discussion purposes, the present method is described herein with reference to contact-less monitoring of a sleeping person. To that end, at step 302, the designated space is monitored using the range-controlled radar coupled to one or more antennas that are configured to constrain a field of the radar to one or more portions of the designated space, specifically the portion where the subject is asleep.

Accordingly, in one embodiment, the range-controlled radar transmits low power, short duration pulses, for example of about 10 microseconds, at a radio frequency of about 5.8 gigahertz towards the desired portions of the designated space at selected time intervals, for example, every ten milliseconds. These pulses, although thousands of times weaker than those produced by a common cell phone or baby monitor, penetrate the clothing over the sleeping subject and reflect off of the torso to accurately detect micro movements associated with the heart, lungs and thorax portions of the body.

The radar then receives and communicates the reflected signals to a processing unit, such as the processing unit 116 of FIG. 2, coupled to the radar for further processing. In certain embodiments, the radar includes circuitry to store and process the reflected signals using embedded digital signal processing algorithms. Particularly, at step 304, the radar non-invasively monitors the sleeping subject to detect a presence of one or more motion parameters including one or more activity levels and one or more physiological parameters such as heartbeat and respiration using the reflected radar signals.

At step 306, the processing unit 116 determines one or more patterns in the motion parameters detected over a designated period of time (designated motion period of time). In certain embodiments, for example, the processing unit 116 identifies the presence of motion outside designated limits during sleep as anomalous behavior. To that end, the designated limits may be pre-programmed into the system, input by a user or learned by the system over a period of time. The processing unit 116 extracts gross motion data from the received signals, for example, based on corresponding frequency band characteristics. In one embodiment, for example, the processing unit 116 employs the filter element 216 to generate a signal frame of a particular time duration from the reflected radar signals. Further, the filter element 216 generates the motion or high band frame, for example, corresponding to a signal of about 4 Hz to about 10 Hz for evaluation.

In certain embodiments, the processing unit 116 further extracts statistical, spectral and/or temporal features from the extracted frames. The processing unit 116 then determines the time, the duration and the frequency of motion from the extracted motion frames. The determined time, the duration and the frequency of motion are then used to determine patterns in the detected motion parameters that provide an indication of the nature and/or the extent of the anomalous behavior exhibited by the subject 102. Particularly, the nature and extent of the anomalous behavior identified using the determined patterns allows the processing unit 116 to determine if the person is suffering from a specific health condition, such as restless leg syndrome (RLS) or periodic limb movement disorder (PLMD).

At step 308, the processing unit 116 further determines one or more patterns in the physiological parameters detected over a designated period of time (designated physiological period of time). To that end, the processing unit 116 extracts heartbeat and respiration data along with gross motion from the generated signal frames. Presence of gross motion, however, may corrupt heartbeat and respiration movements. Accordingly, in certain embodiments, the processing unit 116 identifies and extracts data corresponding to physiological parameters such as heartbeat and respiration from the received signals only if no gross motion is detected. Specifically, in one embodiment, the radar measures a "ballistogram" that corresponds to a motion transferred to the surface of the body of the subject due to movements inside the body. By way of example, during each heartbeat, the heart mechanically changes shape, pushing blood into the aorta and out to the arteries. Some of the motion caused by the beating heart appears on the surface of the body, particularly on the chest or thorax and can be measured. Similarly, respiration causes the chest to expand or contract due to the contraction of the diaphragm and the subsequent filling of the lungs during breathing.

The radar detects and communicates the movement of the chest or thorax to the processing unit 116. Further, the processing unit 116 processes the received signals to remove unwanted interference and noise, and then digitally separates, filters and processes the signals to a digital format that contains accurate heart and respiration rates based on corresponding frequency characteristics. Particularly, in one embodiment, the processing unit filters and samples the received signals to generates a signal frame of a particular duration of time. The processing unit 116 then extracts heartbeat and respiration signal data from the generated signal frame based on their corresponding frequency band characteristics. Typically, resting heartbeat rates vary, for example, from about 60 to about 100 beats per minute (about 1.0 to 1.6 Hz), while the respiration rates vary from about 12 to about 20 breaths per minute (about 0.2 to 0.35 Hz).

By way of example, the processing unit 116 extracts a respiration frame of about 30 seconds from the signal frame generated from the received signals. Additionally, the processing unit generates heartbeat frames of about 10 seconds and motion frames of about 5 seconds from the signal frame. To that end, in one embodiment, the processing unit, for example, employs a filter with a transition between ~0.70 Hz and ~3.5 Hz to isolate heartbeats from the signal frame. In certain instances, however, the heartbeat respiration and motion signals may overlap with each other in the received signals. Accordingly, the processing unit evaluates such frames at a more frequent rate, such as about every second. Further, in certain embodiments, the processing unit generates sliding time frames by discarding the earliest 1 second and includes the most recent 1 second while keeping the total frame durations same.

In embodiments where the heartbeat and respiration frames are extracted along with the gross motion frames, the processing unit 116 adjusts the heartbeat and respiration data to account at least in part for the variations caused due to the gross motion. In one embodiment, for example, the processing unit assigns higher weights or confidence levels to physiological parameters detected in absence of gross motion than the parameters detected in presence of gross motion. The processing unit may also adjust the detected motion, heartbeat and respiration parameters in view of additional parameters such as ambient environmental conditions and variations in the subject's activity levels that are independent of the health condition of the subject.

By way of example, the ambient sound and temperature may affect the subject's respiration and sleep duration. Similarly, the subject's physiological parameters may be affected if the subject has a pre-existing health condition, begins exercising or starts use of a new medicine. The processing unit 116 adapts the detected motion, heartbeat and respiration values to account for variations caused by such external parameters, for example, by assigning appropriate weights to the motion and physiological parameters. The specific weights assigned may be input by a user during use, preprogrammed into the system 100 or learned over a period of time.

The processing unit 116 then uses these additional parameters and/or adjusted values of the determined motion and physiological parameters to determine patterns in the detected physiological parameters that are indicative of specific health conditions. Particularly, in one embodiment, the processing unit 116 determines specific characteristics or patterns in these weighted, adjusted and/or actual values determined over a designated period of time, for example, a day, a week or a month. Further, at step 310, the processing unit 116 assesses a health condition of the subject based on the determined patterns of the motion parameters and/or the physiological parameters measured over the designated motion and/or physiological period of time. It may be noted that in certain embodiments, the designated motion period of time can be same as the designated physiological period of time, while in certain other embodiments, the designated motion period of time can be different from the designated physiological period of time. The processing unit 116, in one embodiment, compares the determined characteristics and patterns with stored motion, heartbeat and/or respiration patterns indicative of potential health conditions. The processing unit 116 uses the comparison to identify if the subject is suffering from a specific ailment such as apnea, arrhythmia or sleep disturbance.

In one embodiment, for example, the processing unit 116 determines sleep latency of the subject by detecting a pattern in the duration of time it takes the subject to fall asleep, for example, measured over a month. Here, the sleep and awake states may be identified, for example, simply based on periods of no or negligible motion and presence of gross motion, respectively. Further, the processing unit may also determine sleep efficiency using a ratio of time spent by the subject in sleep to the time spent in bed awake indicated by the presence of motion. The processing unit 116 may also identify patterns in the sleep and wakeup cycles of the subject to determine if the subject suffers from sleep fragmentation.

Additionally, the processing unit 116 identifies specific characteristics and patterns in the respiration values measured over the designated period of time to determine if the subject is suffering from bradypnea, tachypnea or apnea. Similarly, the processing unit 116 uses the determined heart rate patterns to identify underlying health conditions such as bradycardia, tachycardia and arrhythmia.

In certain embodiments, if the processing unit 116 determines that the subject's heartbeat and/or respiration is outside their designated threshold limits, the processing unit 116 generates an alarm to notify appropriate personnel or health monitoring system of a potential medical condition. In certain embodiments, however, the processing unit 116 terminates the alert and restores the system to a default configuration upon detecting motion and/or determining an increase in values of the one or more parameters above their corresponding threshold limits.

The health monitoring systems and methods disclosed hereinabove, thus, provide a non-contact, inexpensive and efficient technique for monitoring and evaluating the health of a subject. In particular, the present systems employ fast and simple computations that evaluate the subject's motion and vital signs to identify if the subject is suffering from an illness and generate an appropriate alert or log the measured data for later evaluation and reporting. Particularly, the system employs techniques that either ignore or account for variations in heartbeat and respiration estimates measured in presence of gross motion. The system accounts for variations in external parameters such as temperature, noise and/or the subject's mental state or known health condition. The system, thus, uses the heartbeat and respiration values measured in absence of motion and adapted in view of external parameters to make a more accurate and early assessment of the subject's health.

In certain embodiments, the present system and methods may also be used to monitor the efficacy of a drug or medicine being administered to the subject. Similarly, effect of a new physical activity or other stimulus may be identified and adapted to benefit the subject's health. Such continual evaluation may be used for identifying factors that can be used to promote sleep and health in infants and adults. The uncomplicated processing employed by the present methods and systems allows for use of standard-processing devices, thereby reducing equipment cost and complexity. Further, the detection of the physiological parameters is greatly facilitated by the use of range-controlled radar that can penetrate through most obstructing objects in the field of view of the system. Moreover, employing the range-controlled radars eliminates the need to store images and/or other personally identifiable information, thus mitigating privacy concerns.

Although the exemplary embodiments of the present system disclose the use of range-controlled radar circuitry, use of any other suitable type of motion sensing devices, such as electromagnetic, acoustic or optical measurement devices for monitoring a subject in a resting state is also contemplated.

Furthermore, the foregoing examples, demonstrations, and process steps such as those that may be performed by the processing units 116 may be implemented by suitable code on a processor-based system, such as a general-purpose or special-purpose computer. It should also be noted that different implementations of the present technique may perform some or all of the steps described herein in different orders or substantially concurrently, that is, in parallel. Furthermore, the functions may be implemented in a variety of programming languages, including but not limited to Python, C++ or Java. Such code may be stored or adapted for storage on one or more tangible, machine readable media, such as on data repository chips, local or remote hard disks, optical disks (that is, CDs or DVDs), or other media, which may be accessed by a processor-based system to execute the stored code.

While only certain features of the present invention have been illustrated and described herein, many modifications and changes will occur to those skilled in the art. It is, therefore, to be understood that the appended claims are intended to cover all such modifications and changes as fall within the true spirit of the invention.

The invention claimed is:

1. A method for monitoring a subject, comprising:
monitoring a subject in a resting state using a monitoring system operationally coupled to one or more range-controlled radars, wherein the range-controlled radars are configured to constrain one or more signals to a designated space where the subject is resting;
non-invasively detecting one or more motion parameters, one or more physiological parameters, or combinations thereof, corresponding to the subject using the one or more signals received from the range-controlled radars, wherein the motion parameters comprise one or more activity levels and the physiological parameters comprise one or more of heartbeat and respiration;
determining one or more patterns in the motion parameters detected over a designated motion period of time using the monitoring system;
assigning one or more weighted values to one or more actual values corresponding to the physiological parameters if physiological parameters are detected in presence of motion parameters over a designated physiological period of time using the monitoring system;
determining one or more patterns in the weighted values corresponding to the physiological parameters if the physiological parameters are detected in presence of the motion parameters using the monitoring system;
determining one or more patterns in the actual values corresponding to the physiological parameters if the physiological parameters are detected in absence of the motion parameters using the monitoring system; and
assessing a health condition of the subject based on the determined patterns in the motion parameters, the determined patterns in the weighted values corresponding to the physiological parameters, the determined patterns in the actual values corresponding to the physiological parameters, or combinations thereof.

2. The method of claim 1, wherein non-invasively detecting one or more physiological parameters comprises:
processing the received signals to extract components corresponding to one or more frequency bands, wherein each frequency band corresponds to a particular physiological parameter; and
determining one or more characteristics corresponding to the one or more physiological parameters based on the corresponding frequency band components.

3. The method of claim 1, wherein non-invasively detecting one or more motion parameters comprises:
processing the received signals to extract components corresponding to one or more frequency bands, one or more amplitudes, or combinations thereof, wherein one or more specific frequency bands and amplitudes correspond to a particular motion parameter; and
determining one or more characteristics corresponding to the one or more motion parameters based on the corresponding frequency band and amplitude components.

4. The method of claim 1, wherein assessing a health condition of the subject comprises determining the presence of motion parameters as indicators of sleep disturbance.

5. The method of claim 1, wherein assessing a health condition of the subject comprises ignoring values of the detected physiological parameters on determining the presence of motion parameters corresponding to the subject.

6. The method of claim 1, wherein assessing a health condition of the subject comprises assigning a designated weighted value to the physiological parameters detected in view of one or more of a known health condition, ambient environmental conditions and determined activity levels.

7. The method of claim 1, wherein assessing the health condition of the subject comprises matching the determined patterns corresponding to the detected physiological parameters to stored patterns corresponding to known health conditions.

8. The method of claim 1, wherein assessing the health condition of the subject comprises:
determining a known health condition of the subject;
determining ambient environmental conditions corresponding to the subject;
determining an activity level of the subject when awake; and
identifying the health condition of the subject based on based on the determined patterns of the motion parameters, the physiological parameters, or combinations thereof, in view of one or more of the known health condition, the ambient environmental conditions and the determined activity level.

9. The method of claim 1, wherein assessing the health conditions of the subject comprises:
detecting changes in values of the detected heartbeat over the designated physiological time period; and
identifying the health condition associated with the subject as one of bradycardia and tachycardia based on the detected changes.

10. The method of claim 1, wherein assessing the health conditions of the subject comprises:
detecting changes in values of the detected respiration over the designated physiological time period; and
identifying the health condition associated with the subject as one or more of bradypnea, tachypnea, and apnea based on the detected changes.

11. The method of claim 1, wherein assessing the health conditions of the subject comprises:
detecting changes in values of the detected motion parameters over the designated motion time period; and
identifying the health condition associated with the subject as one or more of restless leg syndrome, periodic limb movements disorder and insomnia based on the detected anomalous changes.

12. The method of claim 1, wherein assessing the health conditions of the subject comprises:
detecting changes in values of one or more motion parameters outside corresponding designated limits over the designated motion time period;
detecting changes in values of one or more physiological parameters outside corresponding designated limits over the designated physiological time period; and
identifying the health condition associated with the subject based on the detected changes in one or more of the motion parameters and the physiological parameters over corresponding designated limits.

13. The method of claim 1, further comprising generating an audio output, a visual output, an alert message, or combinations thereof, upon determining that values of the detected physiological parameters are outside corresponding thresholds.

14. The method of claim 13, further comprising terminating the generated audio output, the visual output, the alert message, or combinations thereof, upon determining that values of the detected physiological parameters are within corresponding thresholds.

15. A system for non-contact monitoring of a subject, comprising:
one or more range-controlled radars configured to transmit a radar signal and receive a reflected radar signal from the subject in a resting state, wherein the range-controlled radars are configured to constrain the transmitted radar signal to a designated space where the subject is resting;
at least one processing unit communicatively coupled to the one or more range-controlled radars such that the processing unit is configured to:
non-invasively detect one or more motion parameters, one or more physiological parameters, or combinations thereof, corresponding to the subject using the reflected radar signal, wherein the motion parameters comprise one or more activity levels and the physiological parameters comprise one or more of heartbeat and respiration;
automatically deactivate the one or more range-controlled radars if the motion parameters, the physiological parameters, or combinations thereof, are determined to be absent during a designated period of time;
determine one or more patterns in the motion parameters detected over a designated motion period of time;
assign one or more weighted values to one or more actual values corresponding to the physiological parameters if physiological parameters are detected in presence of the motion parameters over a designated physiological period of time;
determine one or more patterns in weighted values corresponding to the physiological parameters if the physiological parameters are detected in presence of the motion parameters;
determine one or more patterns in the actual values corresponding to the physiological parameters if the physiological parameters are detected in absence of the motion parameters;
assess a health condition of the subject based on the determined patterns in the motion parameters, the determined patterns in the weighted values corresponding to the physiological parameters, the determined patterns in the actual values corresponding to the physiological parameters, or combinations thereof; and
a data repository coupled to the processing unit, wherein the data repository stores one or more of the reflected radar signal data, the motion parameters, the physiological parameters, the determined patterns, or combinations thereof.

16. The system of claim 15, further comprising timing circuitry coupled to the processing unit, wherein the timing circuitry determines a duration of time corresponding to a presence of one or more physiological parameters, one or more motion parameters, or a combinations thereof.

17. The system of claim 15, further comprising an alerting system coupled to one or more of the processing unit, wherein the processing unit configures the alerting system to generate an audio output, a visual output, an alert message, or combinations thereof, upon determining the health condition of the subject.

18. The system of claim 15, further comprising one or more sensors coupled to at least one of the range-controlled radar system and the processing unit, wherein the sensors measure one or more of an ambient temperature, humidity, sound level and the subject's body temperature.

19. A non-transitory computer readable medium that stores instructions executable by one or more processors to perform a method for monitoring a subject, comprising:
monitoring a subject in a resting state using one or more range-controlled radars, wherein the range-controlled radars are configured to constrain one or more signals to a designated space where the subject is resting;
non-invasively detecting one or more motion parameters, one or more physiological parameters, or combinations thereof, corresponding to the subject using the one or more signals received from the range-controlled radars, wherein the motion parameters comprise one or more activity levels and the physiological parameters comprise one or more of heartbeat and respiration;
automatically deactivating the one or more range-controlled radars if the motion parameters, the physiological parameters, or combinations thereof, are determined to be absent during a designated period of time;
determining one or more patterns in the motion parameters detected over a designated motion period of time;
assigning one or more weighted values to one or more actual values corresponding to the physiological parameters if physiological parameters are detected in presence of motion parameters over a designated physiological period of time;
determining one or more patterns in the weighted values corresponding to the physiological parameters if the physiological parameters are detected in presence of the motion parameters;
determining one or more patterns in the actual values corresponding to the physiological parameters if the physiological parameters are detected in absence of the motion parameters; and
assessing a health condition of the subject based on the determined patterns in the motion parameters, the determined patterns in the weighted values corresponding to the physiological parameters, the determined patterns in the actual values corresponding to the physiological parameters, or combinations thereof.

20. The non-transitory computer readable medium of claim 19, wherein the instructions executable by the one or more processors automatically activate the one or more range-controlled radars if the motion parameters, the physiological parameters, or a combination thereof, are detected subsequent to the automatic deactivation during the designated monitoring period of time.

* * * * *